United States Patent [19]

Kamewada

[11] Patent Number: 5,543,972
[45] Date of Patent: Aug. 6, 1996

[54] MIRROR FOR PRODUCING A DEVELOPMENT PICTURE OF THE WALL OF A BOREHOLE IN THE GROUND AND DEVICE THEREFOR

[75] Inventor: Shunichi Kamewada, Sapporo, Japan

[73] Assignee: Raax Co., Ltd., Sapporo, Japan

[21] Appl. No.: 867,226

[22] PCT Filed: Sep. 26, 1991

[86] PCT No.: PCT/JP91/01282

§ 371 Date: Jun. 6, 1992

§ 102(e) Date: Jun. 6, 1992

[87] PCT Pub. No.: WO92/06277

PCT Pub. Date: Apr. 16, 1992

[30] Foreign Application Priority Data

Oct. 9, 1990 [JP] Japan .................. 2-270880
Oct. 25, 1990 [JP] Japan .................. 2-287827

[51] Int. Cl.⁶ .............. G02B 5/08; E21B 47/00; E21B 49/00; G01N 21/00
[52] U.S. Cl. .............. 359/834; 359/868; 359/894; 356/241; 175/49; 175/50; 73/152.01; 33/302; 33/304
[58] Field of Search .............. 359/367, 834, 359/835, 836, 838, 850, 868, 894; 356/241; 73/151; 166/255; 33/302, 304; 175/40, 49, 50

[56] References Cited

U.S. PATENT DOCUMENTS

| 1,655,850 | 1/1928 | Watts ................... 359/726 |
| 1,851,705 | 3/1932 | Herz .................... 359/834 |
| 2,901,943 | 9/1959 | Tackaberry .............. 359/834 |
| 3,597,702 | 8/1971 | Orsay et al. ............ 359/834 |
| 3,610,763 | 10/1971 | Mathews ................ 356/241 |
| 4,184,562 | 1/1980 | Bakamjian .............. 73/622 |
| 4,317,632 | 3/1982 | Orphan et al. .......... 356/241 |
| 4,326,808 | 4/1982 | Pryor et al. ........... 356/445 |
| 4,373,811 | 2/1983 | Jones .................. 359/367 |
| 4,678,321 | 7/1987 | Inokuchi ............... 359/726 |
| 4,899,277 | 2/1990 | Iizuka et al. .......... 356/241 |

FOREIGN PATENT DOCUMENTS

| 0291256 | 11/1935 | Italy ................. 359/831 |
| 61-126292 | 6/1986 | Japan . |
| 62-22035 | 1/1987 | Japan . |
| 1-94192 | 4/1989 | Japan . |
| 1-121492 | 5/1989 | Japan . |
| 1-210594 | 8/1989 | Japan . |
| 2-54086 | 2/1990 | Japan . |
| 2-101283 | 4/1990 | Japan . |
| 2-157391 | 6/1990 | Japan . |
| 2-163638 | 6/1990 | Japan . |

*Primary Examiner*—Ricky D. Shafer
*Attorney, Agent, or Firm*—Oblon, Spivak, McClelland, Maier & Neustadt, P.C.

[57] ABSTRACT

A compound type cone mirror installed inside a sonde moving up and down in a borehole for observing the whole circumference of the hole wall at an arbitrary depth at a time, a combined mirror for locally observing the hole wall in detail, and an elevating sonde equipped with these mirrors are provided for observing the wall surface of a borehole In the ground. In the compound type cone mirror, a transparent truncated cone block the surface of which is finished by polishing is inserted into a concave portion or pierced hole having the same shape as said truncated cone block and formed coaxially in the axial direction in a transparent column block the surface of which is finished by polishing, and said inserting face is a mirror finished face. Moreover, in the combined mirror, a plane mirror slanted upward at 45° to the axial direction is mounted onto the top face of the truncated cone block or column block of the compound type cone mirror.

6 Claims, 15 Drawing Sheets

MIRROR FOR PRODUCING A DEVELOPMENT PICTURE OF THE WALL OF A BOREHOLE IN THE GROUND AND DEVICE THEREFOR

BACKGROUND OF THE INVENTION

1. Technical Field

The present invention relates to an improved tunnelled cone mirror to be installed in a sonde moving up and down in a borehole bored into ground for observing at a time the whole circumference of the wall of the borehole at an arbitrary depth in order to inspect the surface thereof, a compound type cone mirror, a combined mirror for locally observing the hole wall in detail, and an elevating sonde equipped with these mirrors.

2. Background Art

In a geological survey, it is required to know the state of directional continuity of plane elements such as of bedding, joints and cracks. For this reason, during said geological survey, a sonde has hitherto been moved up and down in the borehole, and a borehole television camera installed in said sonde has been used for directly observing the hole wall. However, with said sonde with built-in borehole camera photographing an image of the hole wall reflected at a plane mirror slanted at an angle of 45° to the surface of the hole wall, the range which can be photographed at a time is limited, which makes it difficult to obtain an overall picture of the underground structure in the borehole.

A device as shown in FIG. 23 was developed, wherein the whole circumference of a part of the side wall of a cylindrical elevating sonde (30) is formed as a transparent window (31), a tunnelled cone mirror (131) which has a tunnel-like hole (130) piercing through in the actual direction at the center of a truncated cone block the conical side face of which is mirror finished by plating etc., is mounted inside of the window such that the incident light incoming through said transparent window (31) from the whole circumference of the borehole wall is reflected into the axial direction, a needle azimuth meter (34) is provided on the axis below said cone mirror (131), and further a television camera (36) for taking a photograph of said azimuth meter (34) through said reflected light and said tunnel-like hole (130) is installed above said cone mirror (131).

With this device, however, particularly the maintenance of the cone mirror was difficult. For this reason, an improved type as shown in FIG. 24 is in use, wherein a lower cone (32) which is designed to be readily attached to and detached from the sonde is provided at the tip of the sonde and constitutes a support for said tunnelled cone mirror (131), so that taking-off the cone mirror from the sonde is facilitated. However, both of said sondes have problems as follows:

(1) The conical mirror face of the cone mirror is exposed to the outside and is thus liable to be contaminated and to become scratched.

(2) The television camera and the mirror are separated, and thus aligning both of them in axis, focus, etc. is time-consuming.

(3) The cone mirror is situated at a position where it is liable to be cooled, and thus dewdrops are likely to be formed on its conical mirror face. Further, both of said devices allow to observe the whole circumference of the hole wall rapidly and easily, but on the other hand they are not suitable when it is desired to observe the detailed structure of a part of the wall surface.

SUMMARY OF THE INVENTION

As a result of extensive investigations in view of this situation, according to a first aspect of the invention, there has been devised a cone mirror preventing contaminants etc. from adhering to the conical mirror face, and further an elevating sonde equipped with this mirror is provided in order to facilitate the maintenance.

Namely, a compound type cone mirror according to the invention is characterized in that the cone mirror is installed inside a transparent window portion formed over the whole circumference of a part of the side face of a cylindrical sonde moving up and down in the borehole by means of a support on the ground and has a conical mirror face reflecting the incident light incoming through said transparent window portion from the whole circumference of the surrounding borehole wall into the axial direction of said sonde, a transparent truncated cone block the surface of which is finished by polishing is inserted into a concave portion or pierced hole having the same shape as said truncated cone block and formed coaxially in a transparent column block the surface of which is finished by polishing, and the conical face closely contacting said truncated cone block with the concave portion or pierced hole of the column block is a mirror finished face.

Another compound type cone mirror according to the invention is characterized in that, in said compound type cone mirror, further, a ring member having approximately the same inner diameter as the upper end face of said truncated cone block is mounted with its one end face onto t-he lower end face of said truncated cone block such that its central axis coincides with the central axis of said truncated cone block, the opening at the other end face being blocked up with a transparent or semitransparent cover, and a freely rolling ball being accomodated in the inner portion thereof.

Moreover, according to the invention, the sonde for observing the hole wall Is characterized in that it comprises a cylindrical sonde moving up and down in the borehole by means of a support on the ground, a compound type cone mirror installed inside the transparent window portion formed over the whole circumference of a part of the side face of said sonde and reflecting the incident light incoming through said transparent window portion from the whole circumference of the borehole wall into the axial direction by means of a transparent truncated cone block the surface of which is finished by polishing and which is inserted into a concave portion or pierced hole having the same shape as said truncated cone block and formed coaxially in a transparent column block the surface of which is finished by polishing, the conical face closely contacting said truncated cone block with the concave portion or pierced hole of the column block being formed as a mirror finished face, and a photographing device provided in said sonde and taking a photograph of the reflected image, said photographing device and said compound type cone mirror being assembled to form a unit.

Another one of the sondes according to the invention is further characterized in that, in said sonde, one end face of a ring member having approximately the same inner diameter as the upper end face of said truncated cone block is mounted onto the lower end face of said truncated cone block so that its central axis coincides with the central axis of said truncated cone block, the opening in the other end face being blocked up with a transparent or semitransparent cover, and a freely rolling ball being accomodated in the inner portion thereof.

Moreover, according to a second aspect of the invention, a combined mirror having advantages of both said conventional plane mirror and cone mirror and an elevating sonde equipped therewith have been developed.

Namely, the combined mirror according to the invention is characterized in that, in the hole wall observing mirror being installed inside the transparent window portion formed over the whole circumference of a part of the side face of the cylindrical sonde moving up and down in the borehole by means of a support on the ground and reflecting the incident light incoming through said transparent window portion form the surrounding borehole wall upward in the axial direction of said sonde, a transparent truncated cone block the surface of which is finished by polishing is inserted into a concave portion or pierced hole having the same shape as said truncated cone block and formed coaxially in a transparent column block the surface of which is finished by polishing, the conical face closely contacting said truncated cone block with the concave portion or pierced hole of the column block is formed as a mirror finished face, and further an upwardly slanting plane mirror slanted at 45° to the axial direction is mounted on the top face of said truncated cone block or column block.

Moreover, according to the Invention, the elevating sonde for observing the hole wall is characterized in that it comprises a cylindrical sonde moving up and down in the borehole by means of a support on the ground, a combined mirror with a conical mirror face and a plane mirror being installed Inside a transparent window portion formed over the whole circumference of a part of the side face of said sonde and reflecting the incident light incoming through said transparent window portion from the whole circumference of the borehole wall upward in the axial direction, said combined mirror being formed by a transparent truncated cone block the surface of which is finished by polishing and which is inserted into a concave portion or pierced hole having the same shape as said truncated cone block and formed coaxially in a transparent column block the surface of which is finished by polishing, the conical face closely contacting said truncated cone block with the concave portion or pierced hole of the column block being formed as a mirror finished face, and the plane mirror being slanted at 45° to the axial direction and mounted upwardly slantingly on the top face of said truncated cone block or column block, a photographing device being provided in said sonde for taking a photograph of the reflected image and being provided or not provided with an electromagnetic azimuth sensor, and a needle azimuth sensor being installed below said combined mirror to be photographed by means of the upper photographing device through the central portion at the end face of said combined mirror, and further said photographing device and said combined mirror are assembled to form a unit.

And, in all cases, it is effective to closely attach onto the surface of the plane mirror a transparent protect block the surface of which is finished by polishing and in which the incident light from the side propagates rectilinearly, is reflected at said plane mirror and then propagates rectilinearly upward in the axial direction.

DETAILED DESCRIPTION OF THE PREFERRED EMBODIMENTS

In the following, the invention will be illustrated in more detail.

Figure 1A:
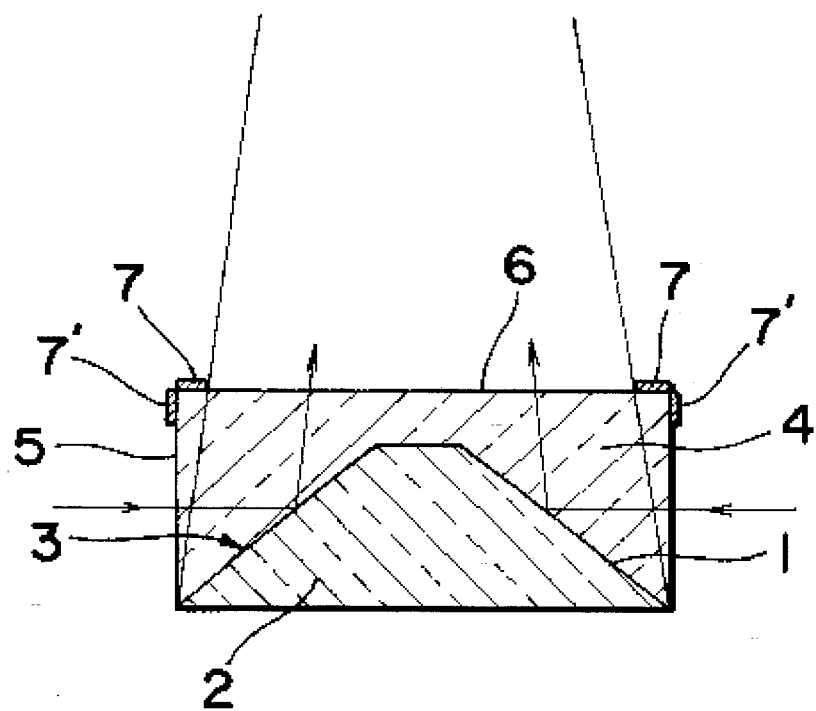
FIGS. 1 (A) and (B) show one example of a compound type cone mirror according to the invention, wherein (A) is a side sectional view and (B) is a top view, FIGS. 2 (A) and (B) show another example of the compound type cone mirror according to the invention, wherein (A) is a side sectional view and (B) is a top view.
Figure 1B:
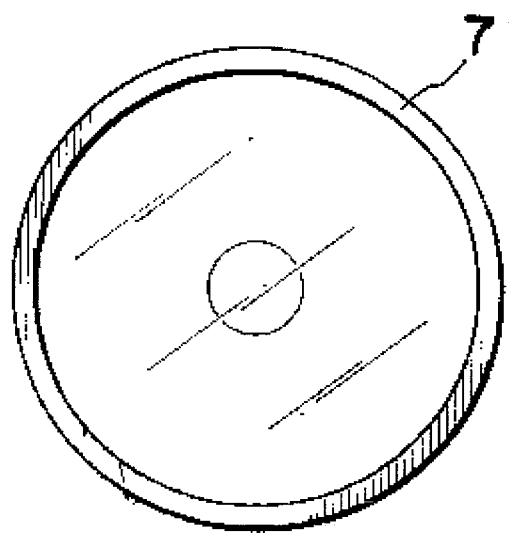

In the unit type cone mirror according to the invention, as shown for example in FIG. 1 (A) and (B), a truncated cone block 2 made of a transparent material such as glass and subjected to a mirror finish processing such as plating etc. on the conical face is inserted into a concave portion 3 of a column block 4 similarly made of transparent material and provided with said concave portion 3 having the same shape as the convex shape of said truncated cone block 2. Incidentally, the mirror finish processing may be omitted on the conical face 1 of the truncated cone bock 2 and may be provided instead on the cone-shaped face of the truncated cone-shaped concave portion 3 of the column block 4.

Since such compound type cone mirror according to the invention is finished by polishing on the side face 5 and the end face 6 of the column block, the light incoming through the side face 5 of the column block from radial direction of said mirror propagates rectilinearly, impinges on the conical face which is mirror finished and is totally reflected, depending on the slanting angle of that conical face, and the reflected light is to propagate through the end face 6 of the column block. Thus, if a photographing device such as a television camera or the like is disposed in front of this reflected light, the whole circumference radially outward of said cone mirror can be photographed at the same time.

Moreover, in the cone mirror according to the invention, the conical mirror face is provided inside of the mirror block unit of the cone mirror, so that contamination, scratching etc. on the mirror finished face can be prevented completely.

Furthermore, since the compound type cone mirror according to the invention is provided with the end face 6 and the side face 5 of the column block 4, it becomes possible to mount said cone mirror and the photographing device installed above this cone mirror as a unit. If the photographing device and the cone mirror constitute a unit in this way, and the photographing device is detached from the sonde, the cone mirror can also be detached from the sonde at the same time, which is advantageous for easy maintenance of the cone mirror. Further, if the photographing device and the compound type cone mirror are coaxially assembled as a unit beforehand, it is also possible to achieve savings of labour for aligning the axis and focus of both devices whenever they are operated.

Besides, at this time, when for example the outer circumferential portion of the end face 6 of the column block is used as the attaching portion 7 as in FIG. 1, all of the ranges of the visual field of the hole wall reflected at the conical face can be covered with the photographing device installed thereabove, by appropriately selecting the angle of the conical face of said cone mirror, as shown in the drawing.

Instead of said attaching portion 7, it is also possible for example to use the outer circumference of the upper end portion of the side face 5 of the column block as attaching portion 7', as in FIG. 1.

Figure 2A:
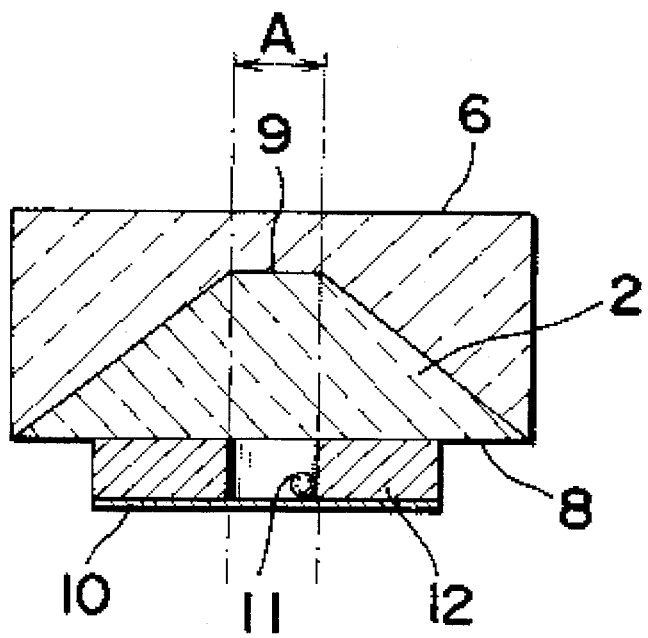
Figure 2B:
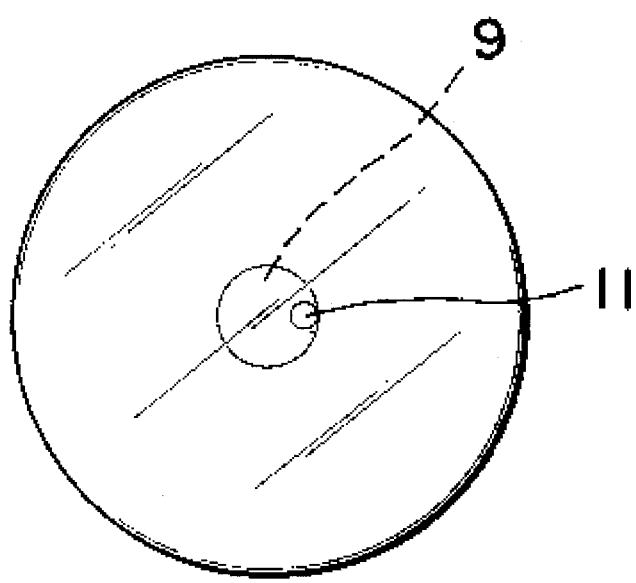

Further, the one end face of a ring member 12 having approximately the same inner diameter as the upper end face 9 of the truncated cone block is mounted onto the lower end face 8 of the truncated cone block of the compound type cone mirror such that the central axis of the ring member and the truncated cone block 2 coincide, as in FIG. 2, and one opening end face is blocked up with a transparent plate cover 10, and a freely rolling ball 11 is accomodated in the inner portion thereof. The reason is that said ball 11 made of steel, stained glass or the like can act as a clinometer.

Namely, if constituting such ball clinometer, said ball 11 is biased in a fixed direction when the axial directions of the sonde and of the compound type cone mirror are made coincident and the sonde descends in a slanted hole. And, the position to which the ball 11 has moved can always be observed by means of the photographing device installed above said cone mirror, through the light transmission path (range A in the diagram) formed along the central axis of the upper end face 9 of the truncated cone block. Hence, if the cover 10 is made transparent and a needle azimuth meter is installed below it, the azimuth can be photographed simultaneously with the photographing device, similarly to conventional fashion. In this way, even when the needle azimuth meter ends up to slant in case of a slanted hole, making it impossible to confirm the azimuth with the photographing device, the vertical downward azimuth in the hole can be known from the position of the ball 1, which makes it possible to control the orientation of the photographing device on the basis of this criterion.

Figure 3:
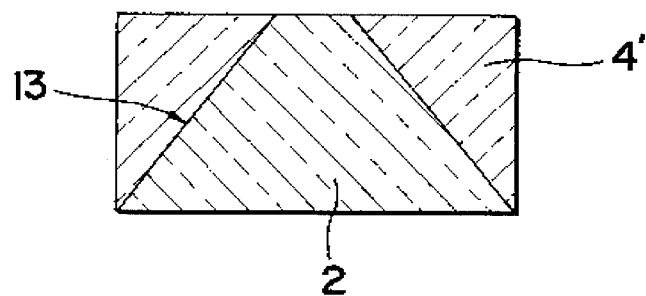
FIG. 3 is a side sectional view showing still another example of the compound type cone mirror according to the invention, FIGS. 4 (A) and (B) show one example of the combined mirror according to the invention, wherein (A) is a side sectional view and (B) is a top view.

Moreover, the compound type cone mirror of the Invention can also have such a constitution that the truncated cone block 2 is inserted into the column block 4' provided with a truncated cone-shaped pierced hole 13 having the same shape as the truncated cone block, as shown in FIG. 3.

Figure 4A:
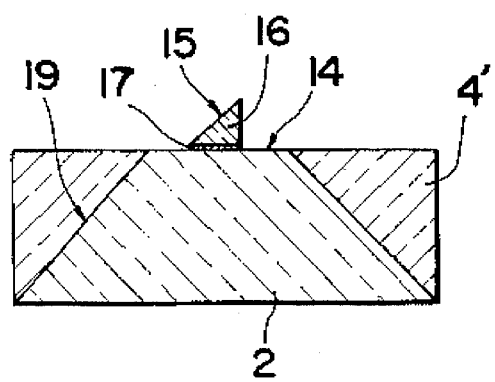
Figure 4B:
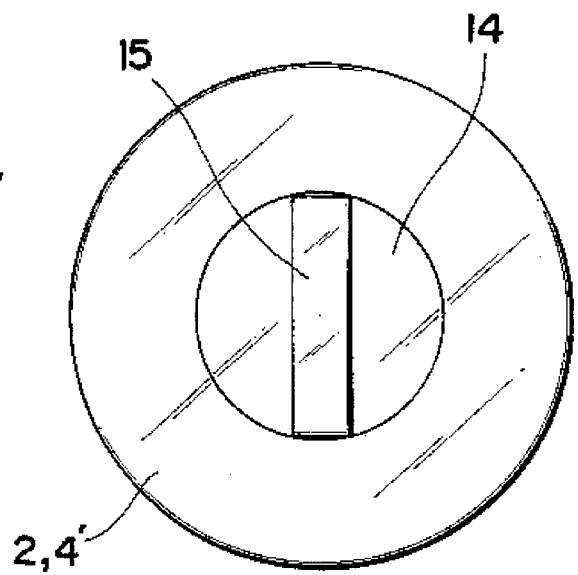

A second example of a combined mirror according to the invention is the following one. As shown in FIG. 4, in the compound type cone mirror wherein a transparent truncated cone block 2 is inserted into a truncated cone-shaped pierced hole provided inside the transparent column block 4', said cone block 2 having the same shape and size as said pierced hole and both conical faces being held in close contact with one another, one side of a triangular column 16 is adhered onto the upper end face 14 of the truncated cone block 2 with a spacer 17 intervening therebetween as shown in FIGS. 4(A) and (B), the other side face of the triangular column being formed as an oblong plane mirror face 15 the length of which falls into a range of width of the small area upper end face (hereinafter referred to as upper end face 14), and said plane mirror 15 is fixed so as to slant upward at an angle of 45°.

Figure 5:
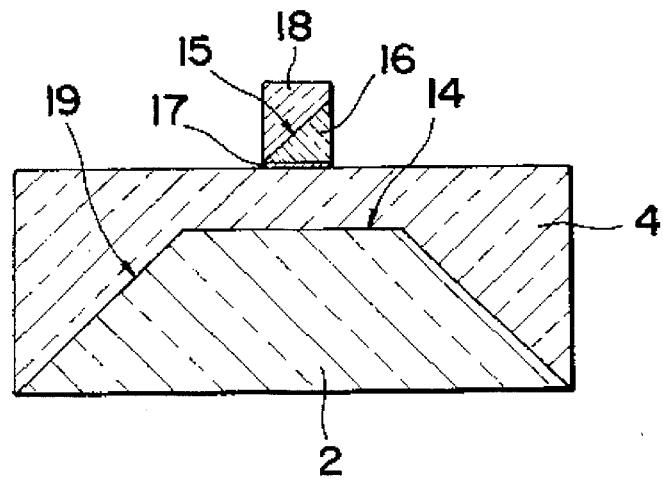
FIG. 5 is a side sectional view showing another example of the combined mirror according to the invention.

Moreover, the invention also includes a combined mirror with the constitution shown in FIG. 5. Namely, in the cone mirror, wherein a transparent truncated cone block 2 with a shape and size equal to those of the truncated cone-shaped concave portion provided along the central axis of the transparent column block 4 as shown in FIG. 1 is inserted into that concave portion to closely contact both conical faces, a plane mirror 15 consisting of a triangular column block 16 the length of which falls within the range of size of said upper end face 14 is mounted at the center of the end face of column block 4 on the side of the upper end face 14 of the truncated cone block 2 in the diametral direction of that end face with a spacer 17 intervening therebetween, similarly to the case of FIG. 4, as shown in FIG. 5. Further, in FIG. 5, such a combined mirror includes also a transparent protect block 18 having a trapezoid or triangular cross section with the same length as said plane mirror 15, the side face and upper face thereof forming respectively an angle of 45° with the face of the plane mirror 15, the protect block being closely contacted with the face of this plane mirror 15.

Besides, in these cone mirrors, at least one of the faces constituting the conical faces, that is, the conical face on the side of the column block 4 or the side of the truncated block 2 is processed into a mirror finished face beforehand.

In these combined mirrors, the column block 4 or 4' protects the conical mirror face 19 which is a conical face processed as a mirror finished face against scratches and contaminants, and providing said block 4 or 4' has the advantage that the combined mirror and the photographing device can easily be assembled into a unit, as described below. Also, said protect block 18 protects the plane mirror 15 against scratches and contaminants.

Further, in all of the combined mirrors, a finish by polishing is required for the light-transmitting surface of the respective transparent members, and the preferred material of which they are made is glass.

Moreover, with such combined mirrors, when they are mounted within the cylindrical sonde similar to the conventional one, the whole circumference of the hole wall can be photographed at a time with the conical mirror face 19 similarly to conventional fashion, and yet, since said plane mirror is provided, a part of the hole wall can be photographed in detail at the same time.

Furthermore, by combining with the azimuth meter similarly to the conventional fashion, it is also possible to photograph at a fixed azimuth.

Besides, for viewing a part of the hole wall In more detail by means of the plane mirror, a zoom lens may be assembled into the photographing camera.

BEST MODE FOR IMPLEMENTING THE INVENTION

In the following, one example of the invention will be illustrated.

EXAMPLE 1

Figure 6:
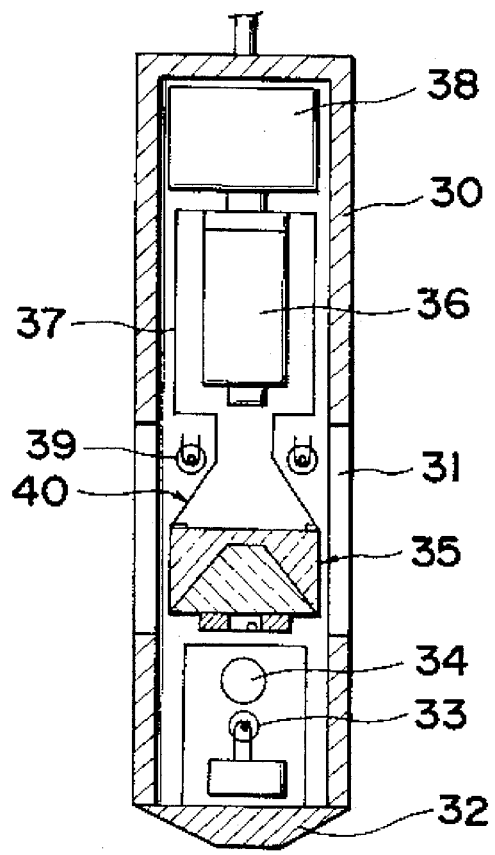
FIG. 6 is a side sectional view showing one example of the sonde for observing the whole wall according to the invention.

As shown in FIG. 6, a part of the side wall of a cylindrical elevating sonde 30 was formed into a transparent window 31 over the whole circumference, and a needle azimuth meter 34 which is always illuminated by a lamp 33 with built-in battery was attached inside a tip bottom cone 32. At the upper portion in the sonde 30, there was fixed the outer circumferential portion of the upper end face 6 of the column block of the compound type cone mirror 35 provided with the ball clinometer as shown in FIG. 2 at the lower end, a housing 37 with a television camera 36 fixedly provided therein was attached coaxially with the central axis of the cone mirror 35, and further, above this, there was internally provided a rotational driving device 38 for said housing 37.

Since the television camera 36 can transmit an image of the whole circumference of the hole wall at a fixed depth to a monitor on the ground surface in real time, if the rotational driving device 38 is operated while the azimuth is confirmed by means of the magnetic needle of the azimuth meter shown in the image, it becomes possible to observe the monitoring picture always with reference to a fixed azimuth. Further, as will be described later, a fixed azimuth picture can be obtained even when recording the real image of the whole circumference of the hole wall as a development picture, which permits a convenient analysis thereafter.

Further, in the sonde 30 shown in FIG. 6, the compound type cone mirror 35 united with the housing 37 is disposed at the position of the transparent window 31, a plurality of light sources 39 for illuminating the hole wall were arranged circumferentially outside the housing above the cone mirror at the position of the transparent window 31 inside the sonde 30. Besides, in order to prevent the light from the light source 39 to enter directly into the television camera 36, the lower portion of the housing 37 was made of a material intransparent for the light of the light source 39 to serve as a shielding hood 40. Since the compound type cone mirror 35 according to the invention is installed in this way inside of the light shielding hood 40 which is warmed up by the light sources 39 for illuminating the hole wall, the formation of dewdrops on the glass surface can be prevented.

Figure 7:
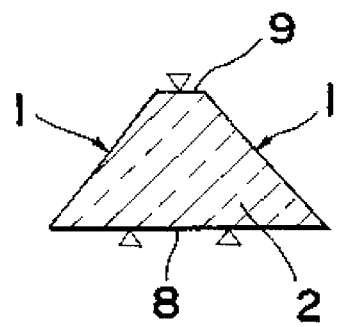
FIGS. 7 through 9 show one example of parts constituting the cone mirror according to the invention, in side sectional views, respectively.
Figure 8:
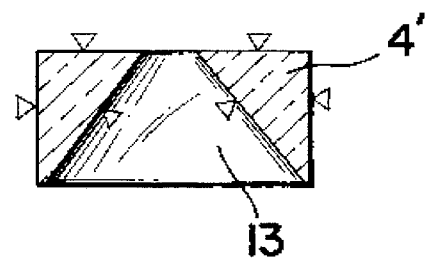
Figure 9:
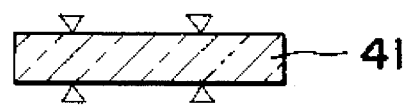

Further, in this example, the compound type cone mirror 35 was fabricated as follows: Namely, the whole circumference of the conical face 1 of the truncated cone block 2 made of glass as shown in FIG. 7 was processed by evaporation plating to form a mirror finished face, and the upper end face 9 and the lower end face 8 were finished by polishing. Then, the glass column block into which this truncated cone block 2 is to be inserted was fabricated from a column block 4' with a truncated cone-shaped pierced hole 13 formed at the central portion thereof as shown in FIG. 8, and from a separate glass plate cap portion shown in FIG. 9 which was closely contacted with the top face of the column block. Besides, the faces finished by polishing are indicated by triangular marks in the diagram.

Method of Producing a Development Picture of the Hole Wall

Here, a specific procedure for obtaining a development picture of the hole wall using the sonde shown in FIG. 6 will be illustrated. The following method is applicable to the fixed azimuth photographing devices used with all cone mirrors disclosed in the invention.

Figure 10:
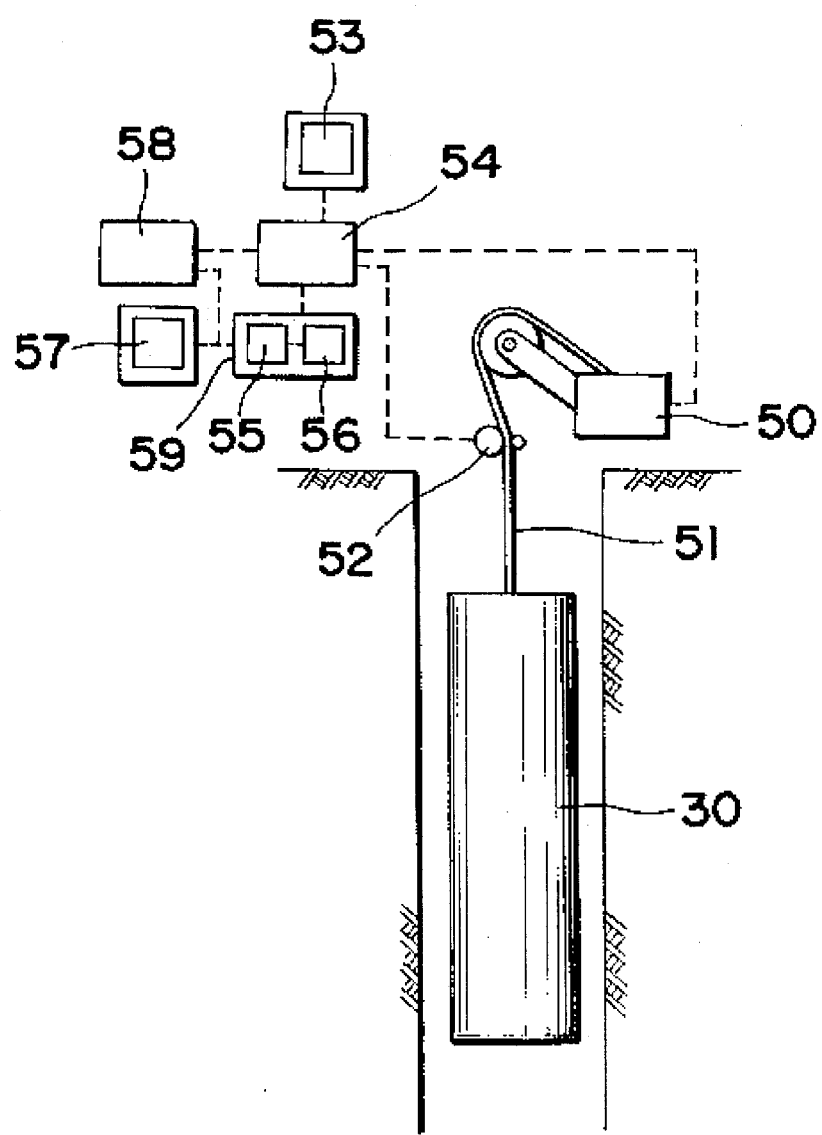
FIG. 10 is a constitution diagram of the device for taking a photograph of the development picture of the hole wall, which device is contained in the sonde according to the invention.

Namely, as shown In FIG. 10, a lifting and dropping device 50 is installed on the ground surface, and a sonde 30 is suspended from said lifting and dropping device by means of a cable 51 and moved up and down in the borehole, and a depth sensor 52 is provided for detecting the movement of said sonde and for generating electric signals at fixed intervals. Further, a television receiver 53 displaying the image signal from the television camera, a sonde controlling device 54, a photographed picture developing device 57 having a photographed picture memory 55 and a development picture memory 56 and producing a development picture in synchronism with the electric signals from the depth sensor 52, and a recording device 58 for recording the photographed picture and the development picture are provided on the ground.

When the sonde 30 with the above constitution is inserted into the hole, a picture of the whole circumference of the hole wall reflected at the conical face of the cone mirror shown in FIG. 2 and a picture of the azimuth meter 34 viewed through the upper end face portion 9 of the truncated cone block provided in the cone mirror are photographed simultaneously with the television camera 36. At this time, the direction of a pointer of the N pole of the azimuth meter is monitored with the television receiver 53, and the direction of the television camera 36 is adjusted by means of the driving device 38 and the sonde controlling device 54 so as to cause said direction to agree with the direction of the magnetic north pole pictured beforehand on the screen of the television receiver 53. When the sonde has been moved up or down by means of the lifting and dropping machine 50 and has thus been moved to a position for producing the development picture, the whole circumferential picture of the hole wall at said position is stored in the photographed picture memory 56 of the photographed picture developing device 39 in synchronism with the electric signals generated by the depth sensor 52 at fixed intervals corresponding to the distance of the sonde, and the electric luminance signals for each pixel are rearranged in the development picture memory 55 to produce the development picture. At this time, fixed azimuth whole circumferential pictures-within a fixed range in the axial direction of the hole wall have been taken ring-wise and input into the photographed picture memory 56, and each pixel of said pictures on the circumference having a center position equivalent to the optical axis of the sonde 30 is picked-up always from a fixed position in a fixed direction and at fixed intervals, and is rearranged linearly in the direction of line in the development picture memory 55 in sequence. Thus, a unit development picture of the hole wall is formed, and the production of said unit development picture is repeated corresponding to the electrical signals generated one after the other in accordance with the movement of the sonde 30, and these unit development pictures are arranged in the direction of row in sequence. Thus, a continuous development picture of the hole wall is produced, which is displayed on a display device 57 for the development picture.

Moreover, if the movement of the sonde is stopped at a particular position in the hole, said developing operation is performed at this position by varying the radius of the circumferential line, and the results are arranged in the direction of row, depending on the size of the radius, and then the development picture at said position can be obtained without movement of the sonde. By repeating this in short time and displaying the results at the same position on the development picture display device, the development picture at said position can be observed as an animation.

This development picture will be illustrated in more detail in conjunction with the drawings.

Figure 11:
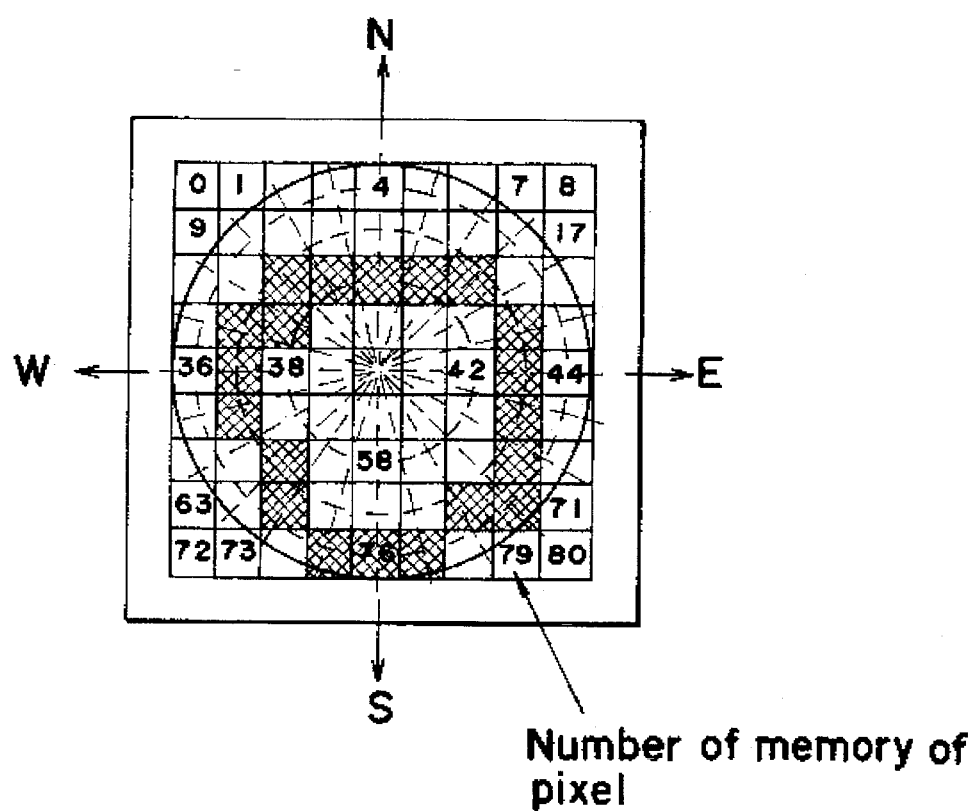
FIG. 11 is an illustration diagram showing one example of the correspondence of pixels of a fixed azimuth whole circumferential picture of the hole wall reflected at the cone mirror, which pixels were stored in the photographed picture memory, to the number of the memory location.

First, FIG. 11 shows one example of the correspondence between the pixels of a fixed azimuth whole circumferential picture of the hole wall as reflected at the cone mirror and the numbers of the memory locations where the pixels are stored in the photographed picture memory.

Figure 12:
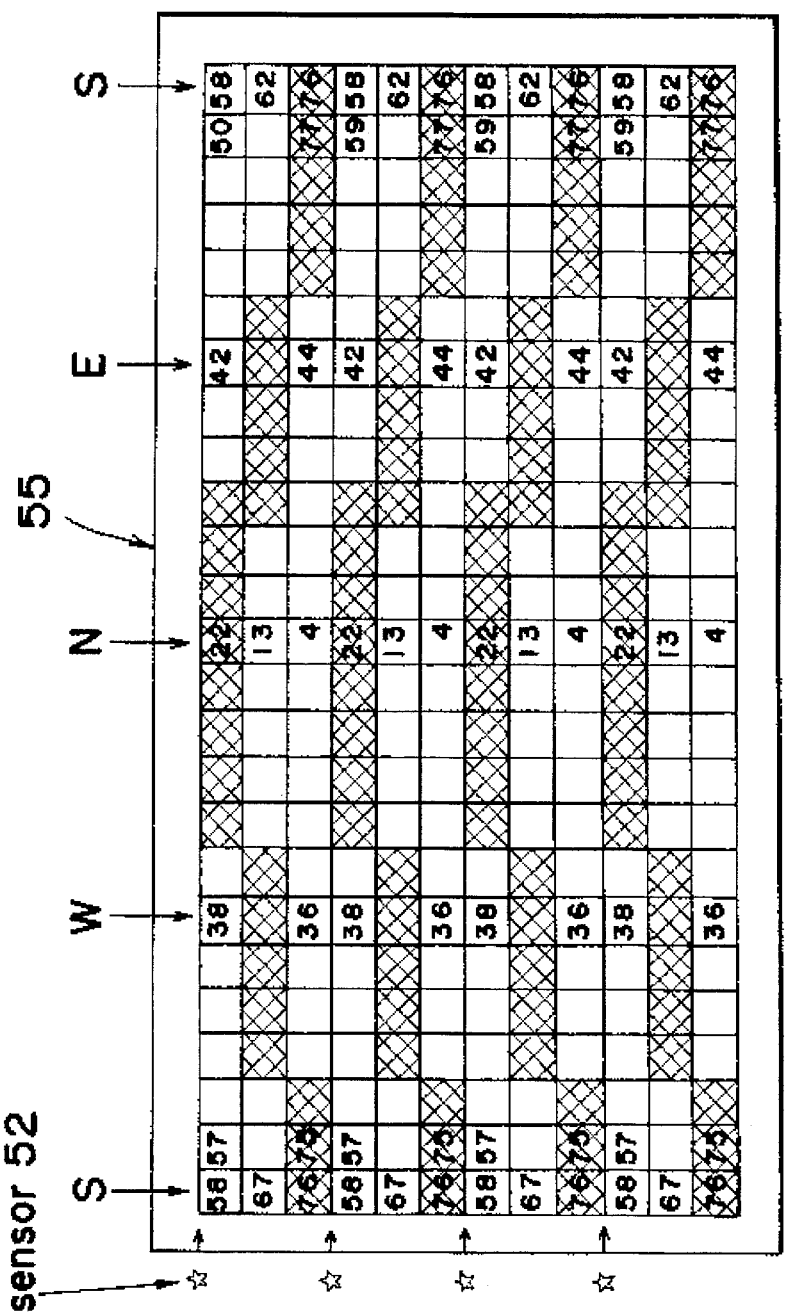
FIG. 12 is an illustration diagram showing a method of developing the picture shown in FIG. 11 over a plurality of lines corresponding to electric signals from a depth sensor and producing the development picture by arranging these in the direction of rows.
Figure 13:
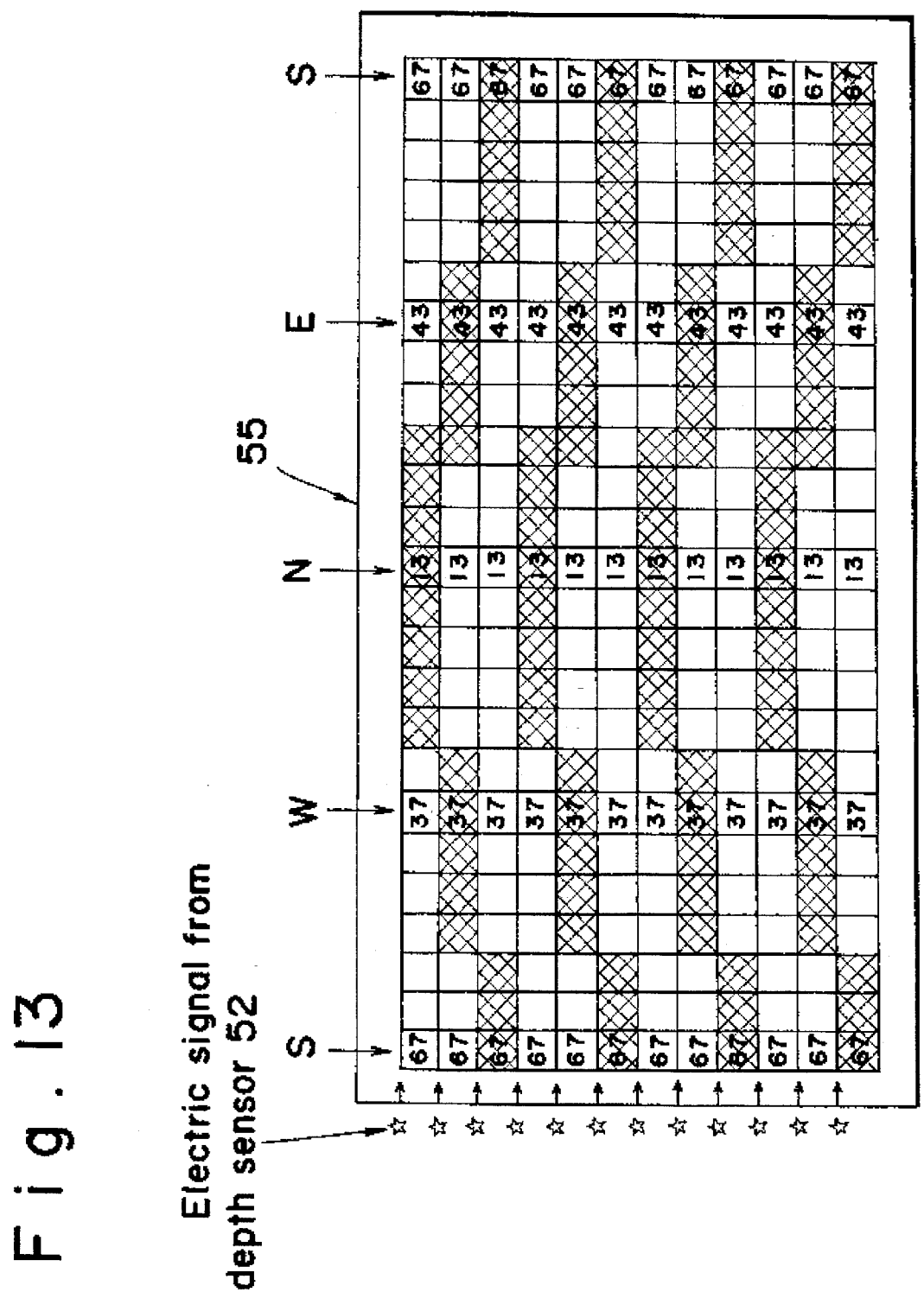
FIG. 13 is an illustration diagram showing a method of developing a picture line by line corresponding to the electric signals from the depth sensor and producing the development picture by arranging these in the direction of rows.

Secondly, examples of the development pictures obtained from this picture are shown in FIG. 12 and FIG. 13.

Namely, in the example shown in FIG. 12, the electric signals are generated from the depth sensor 52 for every movement of the sonde 30 by a fixed distance, and, synchronized therewith, the electric luminance signals of the pixels in the portion which corresponds to the range through which the sonde has moved in this second and which is shown in FIG. 11, are taken in from circumferential lines with different radii in the photographed picture memory 56. These are rearranged to produce a development picture comprising a plurality of lines In the development picture memory 55, and these lines are arranged in the direction of rows corresponding to the movement of the sonde, so that a continuous development picture is produced.

Next, in the example shown in FIG. 13, the electric luminance signal of pixels is taken in from a circumferential line having a fixed radius in the photographed picture memory 56, in synchronism with an electric signal from the depth sensor 52, and this luminance signal is rearranged to produce one line of a development picture in the development picture memory 55. These lines are arranged in the direction of row in accordance with the movement of the sonde, in order to produce a continuous development picture.

The device for producing development pictures of the hole wall as described above has the following advantages.

(1.) Since the whole circumference of the hole wall is photographed simultaneously at a fixed azimuth by means of the cone mirror, there are no sources of error In the relationship between positions in the circumferential direction of the hole, such as in the direction of cracks, and the photographing range in the longitudinal-direction of the hole is constant, regardless of changes in the diameter of the hole and irregularities of the hole wall, so that a continuous development picture can be obtained.

(2.) Since the whole circumferential picture of the hole wall transmitted from the sonde is processed while being monitored, it is possible to immediately respond to changes in azimuth caused by twisting of the cable, etc.

(3.) Since the state of the hole wall can be Judged from the whole circumferential picture of the hole wall supplied by the sonde, the speed of movement of the sonde can be increased in a portion in which it is not necessary to produce a development picture. This results in an efficient survey.

(4.) The device has advantages such as high durability because of the simple structure of the sonde. Moreover, (5.) it is also possible to observe the state of the hole wall by means of an animated development picture and to observe such phenomena as the direction in which ground water springs out In the borehole, the progress of structural looseness, and so on, which phenomena have hitherto been difficult to observe in development pictures.

EXAMPLE 2

Figure 14:
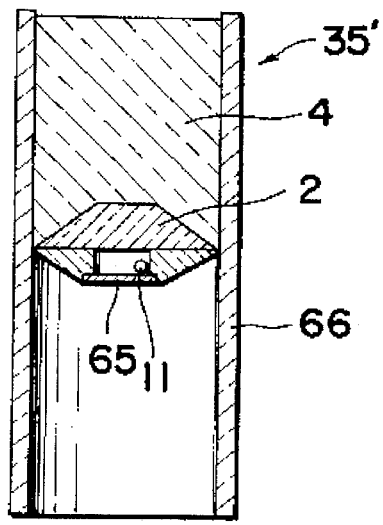
FIG. 14 is a side sectional view showing still another example of the compound type cone mirror according to the invention.

As shown in FIG. 14, a truncated cone block 2 made of transparent glass and mirror-processed on its conical surface was inserted into a concave portion 3 of a column block 4 similarly made of transparent glass, the concave portion having the same shape as the truncated cone, and a ring member 12 was mounted to the lower end face 8 of the truncated cone block. One end face of the ring member was blocked up with a white semitransparent cover 65, a ball 11 being accomodated in the inner portion of the ring member and rolling freely therein. Further, the column block 4 was inserted into one end portion of a transparent glass cylinder 66, thereby constituting a compound type cone mirror 35'.

Figure 15:
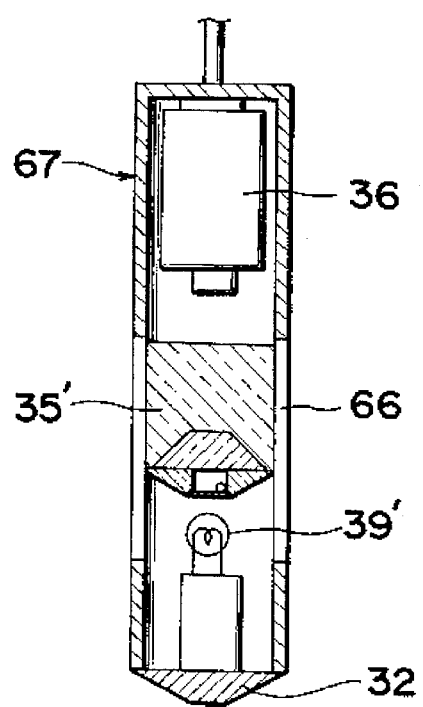
FIG. 15 is a side sectional view showing the sonde used with the compound type cone mirror of FIG. 14.

When using such cone mirror 35', as shown in FIG. 15, the cylindrical member is further extended upward and downward, so that a compound type elevating sonde 67 provided with a lower cone 32 at its lower end is constituted and the transparent cylinder 66 forms the side face of a central portion thereof. A hole wall illuminating light source 39' for illuminating the whole circumference of the surrounding borehole wall is provided inside the sonde 67 at the lower portion thereof, and a photographing television camera 35 is installed at the upper section. Besides, the reason for making the cover on which the ball 11 is rolling white semitransparent in this compound type cone mirror 35 Is that, if it were transparent, the light from the hole wall illuminating light source 39' would directly enter into the camera 36 making it impossible to photograph the most important whole circumferential image of the hole wall. Here, if the cover is made white semitransparent as stated above, the intensity of the light from the light source 39 is decreased and the ball 11 can be photographed as a black shadow. The sonde 67 has the advantage that the overall structure is simple and the outer diameter of the sonde itself can be reduced since the compound type cone mirror 35' is flush with the side face of the sonde 67.

Besides, this sonde 67 is not provided with an azimuth meter. But, for example, by providing a guide rod on the side of a particular azimuth in the slanted hole, and by descending said sonde 67 at a fixed azimuth along this rod, the image over the whole circumference of the hole wall can be photographed at a fixed azimuth.

Figure 16:
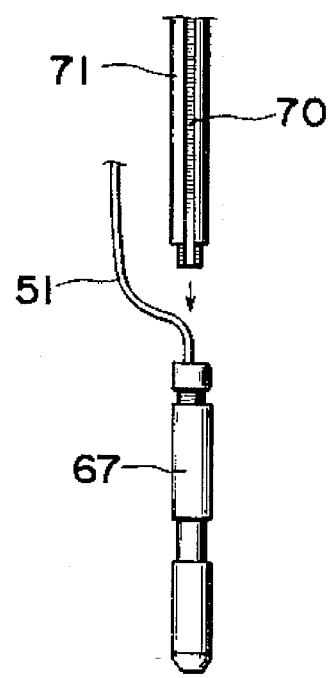
FIGS. 16 and 17 are respective illustration diagrams showing examples of the use of the elevating sonde for observing the hole according to the invention.
Figure 17:
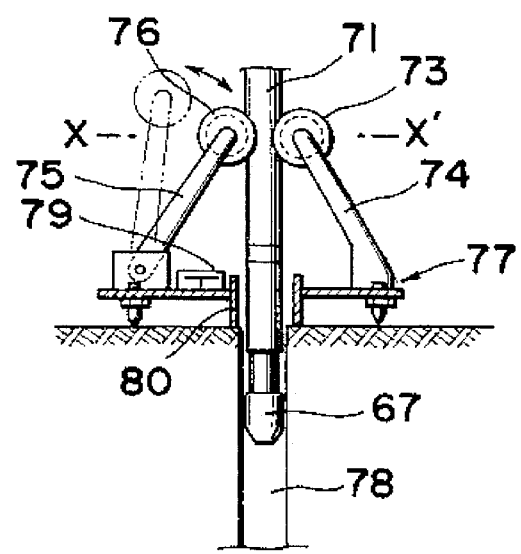
Figure 18:
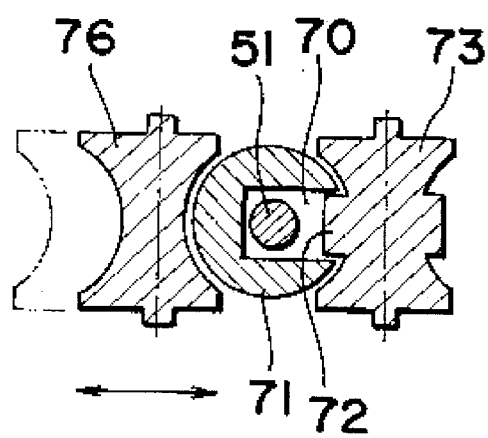
FIG. 18 is a section along the line X–X' in FIG. 17.

Alternatively, fixed azimuth photographing is possible with the method described below. Namely, as shown in FIG. 16, the lower end of a long rod 71 provided with a continuous concave groove 70 in the longitudinal direction of the long round rod is connected to the upper end of said compound type elevating sonde 67 non-rotatably, and the cable 51 of the sonde 67 is extended upward passing in said concave groove 70. Further, as shown in FIG. 17 and FIG. 18, a fixed board 77 having an upwardly projecting fixed supporting arm 74 provided with a convex-center guide roller 73 formed with a convex portion 72 engaging with the concave groove of said long rod 71 and further having a movable roller 76 supported by a movable arm 75 on the opposite side of the borehole 78 to be inspected was installed on the ground. By inserting and descending the long rod 71 with the compound type elevating sonde 67 attached to the lower end thereof into the borehole 78 and passing the long rod between both rollers 73 and 74 of said fixed board 77, the whole circumference of the borehole at a fixed depth can be photographed.

At this time, the azimuth meter 79 is installed on the fixed board 77, so that the direction of the fixed board 77 is specified and thereby the azimuth of the long rod 71 guided by the convex portion 72 of the convex-center guide roller 73 and hence the azimuth of the sonde 67 are also specified. As a result, the sonde 67 moves down at a fixed azimuth making it possible to photograph the whole circumference of the hole wall at a fixed azimuth. Besides, numeral 68 in the drawing designates a lightproof cylinder.

EXAMPLE 3

Next, one example of the elevating sonde used with the combined mirror according to the invention will be described.

Figure 20:
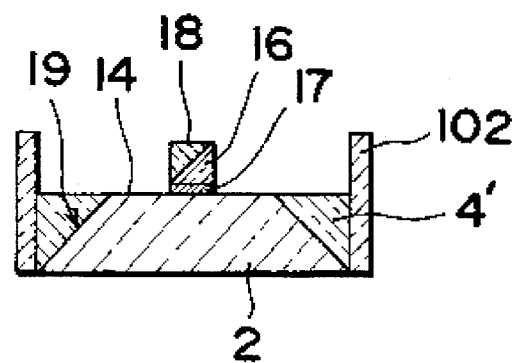
FIG. 20 is a side sectional view showing still another example of a combined mirror according to the invention.
Figure 19:
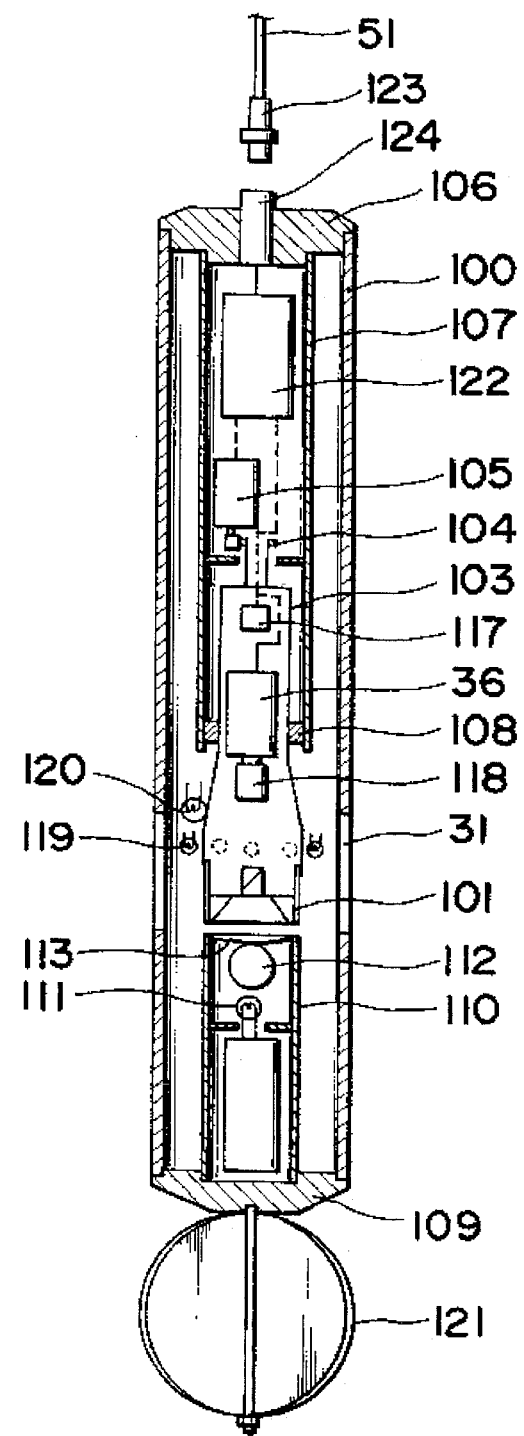
FIG. 19 is a side sectional view showing one example of the elevating sonde with the combined mirror according to the invention installed therein.

As shown in FIG. 19, a combined mirror 101 shown in FIG. 20 was installed at a position inside the transparent window 31 formed over the whole circumference of a part of the side wall in the central portion of a cylindrical elevating sonde 100 suspended at its upper end with a cable 51, the central axis of the combined mirror being arranged in the axial direction of the cylindrical elevating sonde 100 and aligned with the optical axis of the television camera 36 installed in the upper portion of the sonde 100. Namely, as shown in FIG. 20, the combined mirror 100 has such a constitution that a truncated cone block 2 of transparent glass is inserted into a pierced hole of a column block 4' of transparent glass, said pierced hole having the shape of the truncated cone, a protect block 18 with a section of a right-angled isosceles triangle and a triangular column block 16 with a slanting face mirror-processed by plating, both being made of transparent glass and contacted closely to one another with their slanting faces, are adhered onto the exposed upper end face 14 with a spacer 17 intervening therebetween, and further the outer circumferential face of the column block 4' is inserted into the inner circumferential face of a transparent glass cylinder 102 to form a unit.

In this combined mirror 101, the upper end portion of the glass cylinder 102 shown in FIG. 20 is adhered to the lower end of a cylindrical camera-holding cylinder 103 with the television camera 36 internally provided in the upper portion thereof, so that the optical axis of the television camera 36 and the central axis of the combined mirror 101 are aligned with one another. Hence, when taking a photograph of the combined mirror 101 with the television camera 36, the plane mirror 15 always has a fixed positional relationship in that picture.

Next, since the upper end of the camera-holding cylinder 103 is further extended upward, and a rack and pinion gear 104 for rotational driving is mounted to the tip, it can be rotated by means of a driving motor 105. Further, since the camera-holding cylinder 103 is freely rotatably supported by a bearing 108 mounted inside the inner cylinder 107 of the sonde, the outer circumferential face being fixed to the upper cone 106 at the upper end of the elevating sonde 100, when the camera-holding cylinder 103 rotates, its axis of rotation is always aligned with the optical axis of the television camera 36 and the central axis of the combined mirror 101.

Figure 21:
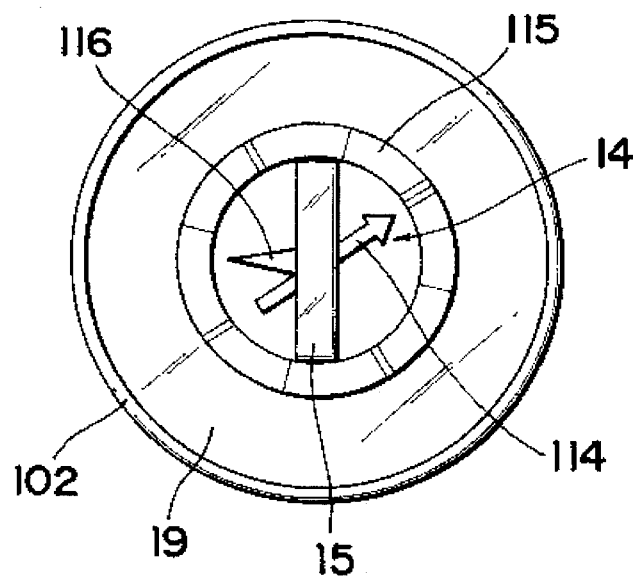
FIG. 21 is an illustration diagram showing the state of the combined mirror in the sonde shown in FIG. 19 if viewed from above.

Moreover, in this elevating sonde 100, a needle azimuth meter 112 provided with an illuminating lamp 111 was installed inside the lower cylinder 110 fixed to the lower cone 109. This needle azimuth meter 112 serves to determine the azimuth of the hole wall surface which is observable with the combined mirror 101 as described below. Namely, by placing the central axis of the needle azimuth meter 112 on the central axis of the combined mirror 101 and by providing a correction lens 113 intervening therebetween, if necessary, as shown in FIG. 21, the magnetic needle 114 of the needle azimuth meter 112 and the azimuth-indicating portion 105 connected to said magnetic needle 114 and freely rotatable therewith can be photographed simultaneously through the upper end face 14 of the truncated cone block 2, when a photograph is taken from above with the television camera 36. If doing so, as shown in FIG. 21, it becomes possible to determine the photographing azimuth of the conical mirror face 19 and the plane mirror 15 of the combined mirror 101 by means of the direction mark 116 showing the photographing direction of the plane mirror 15, which is displayed on the upper end face 14 of the truncated cone block 2, and by means of said azimuth-indicating portion 115 appearing on this upper end face 14, and the magnetic needle 114.

Moreover, when taking a photograph of the whole circumference of the hole wall with the conical mirror face 19 of the combined mirror 101, the needle azimuth meter 112 can be utilized as above. But, if providing an electromagnetic azimuth sensor 117 inside the camera-holding cylinder 103 as shown in FIG. 19, the photographed picture of the whole circumference of the hole wall on the conical mirror face 19 of the combined mirror 101 can be corresponded electrically to a fixed azimuth, which is convenient for processing this picture as an image developed using a fixed azimuth as a criterion.

Furthermore, in order to achieve a more detailed local picture of the hole wall by means of the plane mirror, a zoom lens 118 can also be used as a lens of the television camera 36.

Moreover, illuminating lamps 119 were provided at substantially equal intervals over the whole circumference of the lower end portion of the camera-holding cylinder 103 assembled with the combined mirror 101. These lamps are used when obtaining a picture of the whole circumference of the hole wall by means of the conical mirror face. When obtaining the local picture of the hole wall by means of the plane mirror, a local illuminating lamp 120 may be used which is mounted at the lower end portion of the camera-holding, cylinder 103 in approximately the same direction as the direction of the plane mirror. Besides, in this case, it is also possible to provide such an arrangement that the whole circumferential illuminating lamps 119 as they are or part of said lamps 119 can be used in place of the local illuminating lamp 120.

Besides, numeral 121 in the drawing designates a centering device comprising resilient strips held in circular shape and arranged at right angles relative to one another and with like diameters and mounted to the lower end of the lower cone 109 and aligned with the central axis of the elevating sonde 100. By making the diameter of the centering device 121 approximately equal to the diameter of the borehole wall to be inspected, it is possible to approximately align the central axis of the sonde 100 with the central axis of the borehole constantly during the measurement, while the sonde is moved up and down in the borehole. This alleviates to a great extent such labors as focussing on the hole wall to be photographed.

Also, numeral 122 designates a control unit containing a power source unit inside the sonde, numeral 123 designates a cable connector, numeral 124 designates an upper cone, numeral 106 designates a fixed connector head in the drawing. If the elevating sonde shown in FIG. 19 is used, it is possible to obtain not only the continuous picture developed over the whole circumference in the direction of depth of the borehole wall as described above, but there can also be obtained detailed local continuous pictures as follows:

Namely, the sonde 100 is moved down to a certain depth, the face of the plane mirror 15 at that depth is photographed with the television camera 36, or a magnified image of the face of the plane mirror 15 is photographed by means of the intervening zoom lens 118, this picture of the hole wall is scanned linearly and stored in the photographed picture memory, and then this picture is rearranged in the development picture memory, thus making the unit development picture at a certain point of depth. Thereafter, by combining the unit development pictures obtainable for every fixed distance of movement of the sonde to a continuous sequence in synchronism with the movement of the sonde, very fine geological phenomena can be obtained in the form of continuous pictures in the direction of depth.

EXAMPLE 4

Next, one example of an improved tunnelled cone mirror according to the invention will be described.

Figure 22:
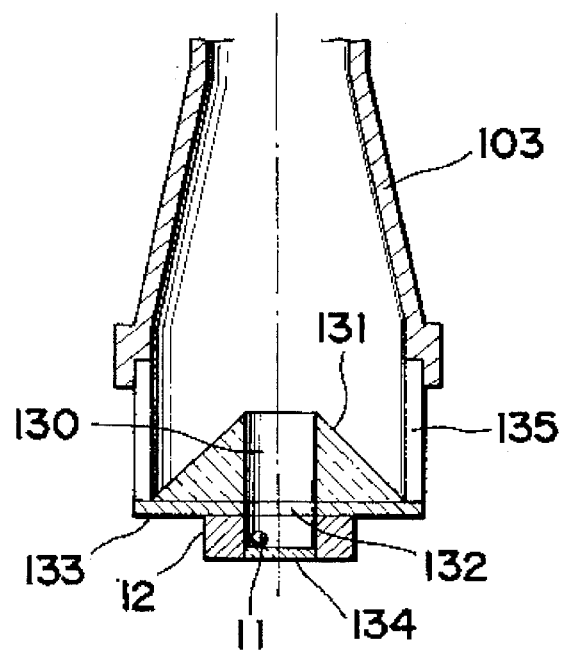
FIG. 22 is a side view showing an improved tunnelled cone mirror according to the invention.
Figure 23:
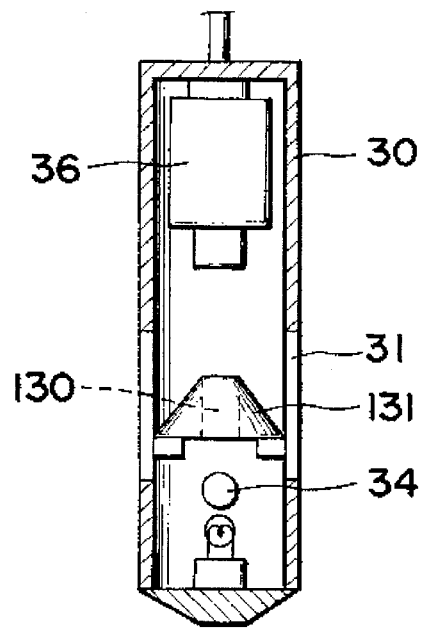
FIGS. 23 and 24 are side sectional views showing conventional elevating sondes for observing the hole wall, respectively.
Figure 24:
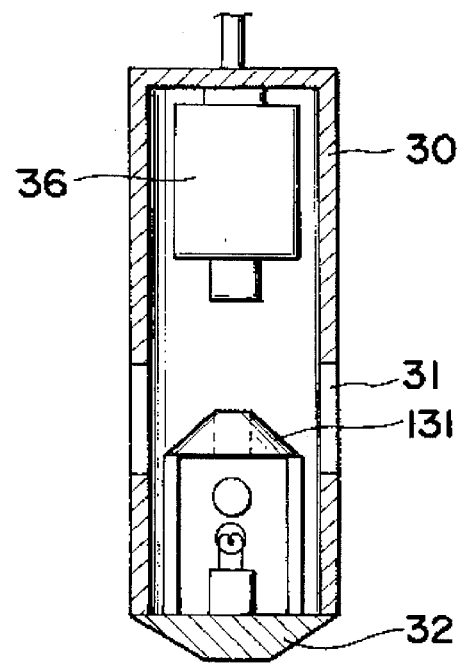

As shown in FIG. 22, a tunnelled cone mirror was fabricated, in which a bottom cover 133 is mounted to the bottom face of the tunnelled cone mirror 131 made of glass and plated on its conical face or made of metal and mirror-processed on its conical face, the bottom cover having a transparent portion 132 with the same diameter as the tunnel hole 130, a ring member 12 having the same inner diameter as said transparent portion 132 and being closed at its lower end face with a transparent or semitransparent window 134 and having a ball 11 accomodated therein is provided on the bottom face of the bottom cover 133, and further one end of a transparent cylinder 135 is fixed to the outer circumferential edge of the bottom cover 133, and the other end of the cylinder is attached to the lower end of the camera-holding cylinder 103.

Since such a tunnelled cone mirror can be combined with the camera to form a unit, difficulties such as focussing and maintenance encountered in photographing the hole wall with the conventional tunnelled cone mirror can be dissolved. Moreover, the ball 11 accomodated in said ring member has the function of a clinometer as described above. In use, such tunnelled cone mirror is installed in the elevating sonde shown in FIG. 6 or FIG. 19.

INDUSTRIAL APPLICABILITY

As described, the compound type cone mirror and the combined mirror according to the invention have various merits in that not only a development picture over the whole circumference of the wall of the borehole bored into the ground can be obtained at a fixed azimuth and further detailed local picture can be obtained simultaneously, but also the device itself can be constituted to be compact and to permit easy maintenance, and the borehole in which it is utilized imposes no problem, even if it is a slanted borehole or the like. The cone mirrors are particularly useful for easily and rapidly exploring the geological phenomena appearing in a borehole.

I claim:

1. A compound type cone mirror device for observing a wall of a borehole, comprising:
    a cylindrical sonde which moves within said borehole along a depth thereof by means of a grounded support;
    a transparent window portion formed over an entire circumference of a portion of a side face of said cylindrical sonde;
    a conical mirror face which reflects incident light incoming through said transparent window portion from an entire circumference of said wall of said borehole into an axial direction of said cylindrical sonde;
    a transparent truncated cone block, a surface of which is finished by polishing, which closely contacts said conical mirror face; and
    a transparent column block, a surface of which is finished by polishing, having a concave portion or a pierced hole of an identical shape as said truncated cone block into which said truncated cone block is inserted, wherein said conical mirror face is a mirror finished face.

2. An elevating sonde for observing a wall of a borehole, comprising:
    a cylindrical sonde which moves within said borehole along a depth thereof by means of a grounded support;
    a transparent window portion formed over an entire circumference of a portion of a side face of said cylindrical sonde;
    a photographing device provided within said cylindrical sonde; and
    a compound type cone mirror installed within said transparent window portion, said compound type cone mirror including:
        a conical mirror face which reflects incident light incoming through said transparent window portion from an entire circumference of said wall of said borehole into an axial direction of said cylindrical sonde;
        a transparent truncated cone block, a surface of which is finished by polishing, which closely contacts said conical mirror face; and
        a transparent column block, a surface of which is finished by polishing, having a concave portion or a pierced hole of an identical shape as said truncated cone block into which said truncated cone block is inserted, wherein said conical mirror face is a mirror finished face and wherein said photographing device and said compound type cone mirror are assembled to form a unit.

3. A combined mirror device for observing a wall of a borehole, comprising:
    a cylindrical sonde which moves within said borehole along a depth thereof by means of a grounded support;
    a transparent window portion formed over an entire circumference of a portion of a side face of said cylindrical sonde;
    a conical mirror face which reflects incident light incoming through said transparent window portion from an entire circumference of said wall of said borehole into an axial direction of said cylindrical sonde;
    a transparent truncated cone block, a surface of which is finished by polishing, which closely contacts said conical mirror face;

a transparent column block, a surface of which is finished by polishing, having a concave portion or a pierced hole of an identical shape as said truncated cone block into which said truncated cone block is inserted; and an upwardly slanting plane mirror mounted on a top face of said truncated cone block or said truncated column block at an angle of 45° with respect to said axial direction of said cylindrical sonde, wherein said conical mirror face is a mirror finished face.

4. A combined mirror device according to claim 3, wherein a transparent protect block a surface of which is finished by polishing and through which light incident from a side thereof propagates rectilinearly, is reflected by said upwardly slanting plane mirror, and then propagates rectilinearly upward in said axial direction of said cylindrical sonde, is closely contacted with a surface of said upwardly slanting plane mirror.

5. An elevating sonde for observing a wall of a borehole, comprising:

a cylindrical sonde which moves within said borehole along a depth thereof by means of a grounded support;

a transparent window portion formed over an entire circumference of a portion of a side face of said cylindrical sonde;

a photographing device provided within cylindrical sonde, wherein said photographing device includes an electromagnetic azimuth sensor;

a needle azimuth sensor; and a combined mirror, said combined mirror including:

a conical mirror face which reflects incident light incoming through said transparent window portion from an entire circumference of said wall of said borehole into an axial direction of said cylindrical sonde;

a transparent truncated cone block, a surface of which is finished by polishing, which closely contacts said conical mirror face;

a transparent column block, a surface of which is finished by polishing, having a concave portion or a pierced hole of an identical shape as said truncated cone block into which said truncated cone block is inserted; and an upwardly slanting plane mirror mounted on a top face of said transparent truncated cone block or said transparent column block at an angle of 45° with respect to said axial direction of said cylindrical sonde, wherein said conical mirror face is a mirror finished face, and wherein said needle azimuth sensor is installed below said combined mirror so as to be photographed by means of said photographing device through a central portion of an end face of said combined mirror, and wherein said photographing device and said combined mirror are assembled to form a unit.

6. An elevating sonde according to claim 5, wherein a transparent protect block a surface of which is finished by polishing and through which light incident from a side thereof propagates rectilinearly, is reflected by said upwardly slanting plane mirror, and then propagates rectilinearly upward in said axial direction of said cylindrical sonde, is closely contacted with a surface of said upwardly slanting plane mirror.

* * * * *

UNITED STATES PATENT AND TRADEMARK OFFICE
CERTIFICATE OF CORRECTION

PATENT NO. : 5,543,972
DATED : August 6, 1996
INVENTOR(S) : Shunichi KAMEWADA

It is certified that error appears in the above-indentified patent and that said Letters Patent is hereby corrected as shown below:

On the title page, Item [86], the PCT information,
It should read:

-- [86] PCT No.: PCT/JP91/01282
   § 371 Date: Jun. 5, 1992
   § 102(e) Date: Jun. 5, 1992 --

Signed and Sealed this

Fifth Day of November, 1996

*Attest:*

BRUCE LEHMAN

*Attesting Officer*  *Commissioner of Patents and Trademarks*